United States Patent [19]
Trikha et al.

[11] Patent Number: 6,046,316
[45] Date of Patent: Apr. 4, 2000

[54] NUCLEIC ACID ENCODING TRUNCATED INTEGRINS

[75] Inventors: Mohit Trikha, Grosse Pointe City; Kenneth V. Honn, Grosse Pointe Woods, both of Mich.

[73] Assignee: Wayne State University, Detroit, Mich.

[21] Appl. No.: 08/987,418

[22] Filed: Dec. 9, 1997

[51] Int. Cl.$^7$ ................................................... C12N 15/12
[52] U.S. Cl. .......................... 536/23.5; 514/44; 435/91.1; 530/395; 530/380
[58] Field of Search ........................ 536/23.5; 530/395, 530/380; 514/44; 435/91.1

[56] References Cited

U.S. PATENT DOCUMENTS

| | | |
|---|---|---|
| 4,683,202 | 7/1987 | Mullis . |
| 5,306,620 | 4/1994 | Ginsberg et al. . |
| 5,523,209 | 6/1996 | Ginsberg et al. . |
| 5,561,047 | 10/1996 | Shattil . |
| 5,594,120 | 1/1997 | Brenner et al. . |
| 5,627,263 | 5/1997 | Ruoslahti et al. . |
| 5,635,527 | 6/1997 | Ono et al. . |

OTHER PUBLICATIONS

Bennett, J.S. et al., "Determinants of the Intracellular Fate of Truncated Forms of the Platelet Glycoproteins IIb and IIIa," *The Journal Of Biological Chemistry* 268(6):3580–3585 (1993).
Block, K.L. et al., "Platelet Glycoprotein IIb Gene Expression as a Model of Megakaryocyte–Specific Expression," *Stem Cells* 13:135–145 (1995).
Boekerche, H. et al., "Platelet–Melanoma Cell Interaction Is Mediated By The Glycoprotein IIb–IIIa Complex," *Blood* 74:658–663 (1989).
Bray, P.F. et al., "Platelet Glycoprotein IIb," *J Clin. Invest.* 80:1812–1817 (1987).
Calvete, J.J., "Clues For Understanding The Structure And Function Of A Prototypic Human Integrin: The Platelet Glycoprotein IIb/IIIa Complex," *Throm. Haemostasis* 72:1–15 (1994).
Chen, Y.Q. et al., "Identification of the $\alpha_{IIb}\beta_3$ Integrin in Murine Tumor Cells," *J. Biol. Chem.* 267:17314–17320 (1992).
Chen, Y.Q. et al., "Ectopic Expression Of Platelet Integrin αIIbβ3 In Tumor Cells From Various Species And Histological Origin," *Int. J. Cancer* 72:642–648 (1997).
Chiang, H.S. et al., "Characterization of integrin expression and regulation on SW–480 human colon adenocarcinoma cells and the effect of rhodostomin on basal and upregulated tumor cell adhesion," *Biochem. et Biophys. Acta* 1224:506–516 (1994).
Clark, E.A. et al., "Integrins and Signal Transduction Pathways: The Road Taken," *Science* 268:233–239 (1995).
*Current Protocols in Molecular Biology*, John Wiley & Sons, NY (1989), 6.31–6.3.6.
Djaffar, I. et al., "A new alternative transcript encodes a 60 kDa truncated form of integrin $\beta_3$," *Biochem. J.* 300:69–74 (1994).

Fitzgerald, L. et al., "Protein Sequence of Endothelial Glycoprotein IIIa Derived from a cDNA Clone," *J. Biol. Chem* 262:3936–3939 (1987).
Frachet, P. et al., "GPIIb and GPIIIa amino acid sequences deduced from human megakaryocyte cDNAs," *Mol. Biol. Rep.* 14:27–33 (1990).
Gulino, D et al., "Expression and purification of a soluble functional form of the platelet αIIβ3 integrin," *Eur. J. Biochem.* 227:108–115 (1995).
Hagman, W. et al., "Activity And Protein Distribution Of 12–Lipoxygenase In Hel Cells: Induction Of Membrane–Association By Phorbol Ester TPA, Modulation Of Activity Of Glutathione And 13–HPODE, And $Ca^{2+}$–Dependent Translocation To Membranes," *Prostaglandins* 46:471–477 (1993).
Heidenreich, R. et al., "Organization of the Gene for Platelet Glycoprotein IIb," *Biochem.* 29:1232–1244 (1990).
Honn, K.V. et al., "$\alpha_{IIb}\beta_3$ Integrin Expression and Function in Subpopulations of Murine Tumors," *Exp. Cell Res.* 201:23–32 (1992).
Hynes, R.O., "Integrins: Versatility, Modulation, and Signaling in Cell Adhesion," *Cell* 69:11–25 (1992).
Kamiyama, M. et al., "Inhibition Of Human Platelet Glycoprotein IIB/IIIA Binding to Fibrinogen by Tumor Cell Membrane Proteins," *Cancer Res.* 53:221–223 (1993).
Lanza, F. et al., "Characterization of the Human Platelet Glycoprotein IIIa Gene," *J. Biol. Chem.* 265:18098–18103 (1990).
Leong, L. et al., "Integrin signaling: roles for the cytoplasmic tails of αIIbβ3 in the tyrosine phosphorylation of pp125$^{FAK}$," *Journal Of Cell Science* 108:3817–3825 (1995).
Maniatis, T., et al., *Molecular Cloning: A Laboratory Manual, Cold Spring Harbor Laboratory Press*, Cold Spring NY, (1982), at pp. 387–389.
O'Toole, T.E. et al., "Modulation of the Affinity of Integrin $\alpha_{IIb}\beta_3$ (GPIIb–IIIa) by the Cytoplasmic Domain of $\alpha_{IIb}$," *Science* 254:845–847 (1991).
O'Toole, T.E. et al., "Integrin Cytoplasmic Domains Mediate Inside–Out Signal Transduction," *J. Cell Biol.* 124:1047–1059 (1994).
Pasqualini, R. et al., "αv Integrins as receptors for tumor targeting by circulating ligands," *Nature BioTechnology* 15(6):5420546 (1997).
Poncz, M. et al., "Structure of the Platelet Membrane Glycoprotein IIb," *J. Biol. Chem.* 262:8476–8482 (1987).

(List continued on next page.)

*Primary Examiner*—Julie Burke
*Assistant Examiner*—Larry R Helms
*Attorney, Agent, or Firm*—Harness, Dickey & Pierce, P.L.C.

[57] ABSTRACT tr-αIIb, a soluble, truncated integrin found to be exclusively expressed in tumor cells is provided. An additional truncated integrin, tr-β3, has also been found to be exclusively expressed in tumor cells. Diagnostic compositions including nucleic acid probes and antibodies and methods for detecting the presence of tr-αIIb and tr-β3 to identify the presence of tumor cells in a sample are also provided.

1 Claim, 11 Drawing Sheets

OTHER PUBLICATIONS

Poncz, M. et al., "Analysis of Rodent Platelet Glycoprotein IIb: Evidence for Evolutionarily Conserved Domains and Alternative Proteolytic Processing," *Blood* 75:1282–1289 (1990).

Prandini, M.H. et al., "Characerization of a Specific Erythromegakaryocytic Enhancer within the Glycoprotein IIb Promoter," *J. Biol. Chem.* 267(15):10370–10374 (1992).

Puerschel, W.Ch. et al., "Immunoreactivity of glycoprotein IIb is present in metastasized but not in non–metastasized primary malignant melanoma," *British J. Dermatol.* 135:883–887 (1996).

Rosa, J.P. et al., "Cloning of Glycoprotein IIIa cDNA From Human Erythroleukemia Cells and Localization of the Gene to Chromosome 17," *Blood* 72:593–600 (1988).

Sambrook J. et al., *Molecular Cloning: A Laboratory Manual*, Second Edition, vol. 2, Cold Spring Harbor Laboratory Press, Cold Spring, NY at pp. 8.46–8.47 (1989).

Sastry, S.K. et al., "Integrin cytoplasmic domains: mediators of cytoskeletal linkages and extra–and intracellular initiated transmembrane signaling," *Current Opin. Cell Biol.* 5:819–831 (1993).

Schwartz, M.A., et al., "Integrins: Emerging Paradigms of Signal Transduction," *Ann. Rev. Cell Dev. Biol.* 11:549–599 (1995).

Shattil, S.J. et al., "Adhesive signaling in platelets," *Current Opin. Cell Biology* 6:695–704 (1994).

Shattil, S.J. et al., "Changes in the Platelet Membrane Glycoprotein IIb–IIIa Complex during Platelet Activation," *J. Biol. Chem.* 260:11107–11114 (1995).

Sosnoski, D.M. et al., "Chromosomal Localization of the Genes for the Vitronectin and Fibronectin Receptors α Subunits and for Platelet Glycoproteins IIb and IIIa," *J. Clin. Invest.* 81:1993–1998 (1988).

Tang, D.G. et al., "Phenotypic Properties Of Cultured Tumor Cells: Integrin $\alpha_{IIb}\beta_3$ Expression, Tumor–Cell–Induced Platelet Aggregation, And Tumor–Cell Adhesion To Endothelium As Important Parameters Of Experimental Metastatis," *Int. J. Cancer* 54:338–347 (1993).

Tang, D.G. et al., "Adhesion Molecules and Tumor Metastasis: An Update," *Invasion Metastasis* 95:109–122 (1994).

Trikha, M. et al., "Contortrostatin, a Snake Venom Disintegrin, Inhibits $\beta_1$ Integrin–mediated Human Metastatic Melanoma Cell Adhesion and Blocks Experimental Metastasis," *Cancer Res.* 54:4993–4998 (1994).

Trikha, M. et al., "Purification And Characterization Of Platelet Aggregation Inhibitors From Snake Venoms," *Throm. Res.* 73:39–52 (1994).

Trikha, M. et al., "Human Prostate Carcinoma Cells Expressed Functional αIIbβ3 Integrin," *Cancer Res.* 56:5071–5078 (1996).

Trikha, M. et al., "The High Affinity αIIbβ3 Integrin Is Involved In Invasion Of Human Melanoma Cells," *Cancer Res.* 57:2522–2528 (1997).

Trikha, M. et al., "Role of αIIbβ3 integrin in prostate cancer metastasis," *Prostate* In Press (1997).

Wippler, J. et al., "The Integrin $\alpha_{IIb}$–$\beta_3$ Platelet Glycoprotein IIb–IIIa, Can Form a Functionally Active Heterodimer Complex without the Cysteine–ric Repeats of the $\beta_3$ Subunit," *The Journal Of Biological Chemistry* 269(12):8754–8761 (1994).

Chang, S.Y. et al., "Analysis Of Integrin mRNA In Human And Roden Tumor Cells," *Biochemical And Biophysical Research Communications* 176(1):108–113 (1991).

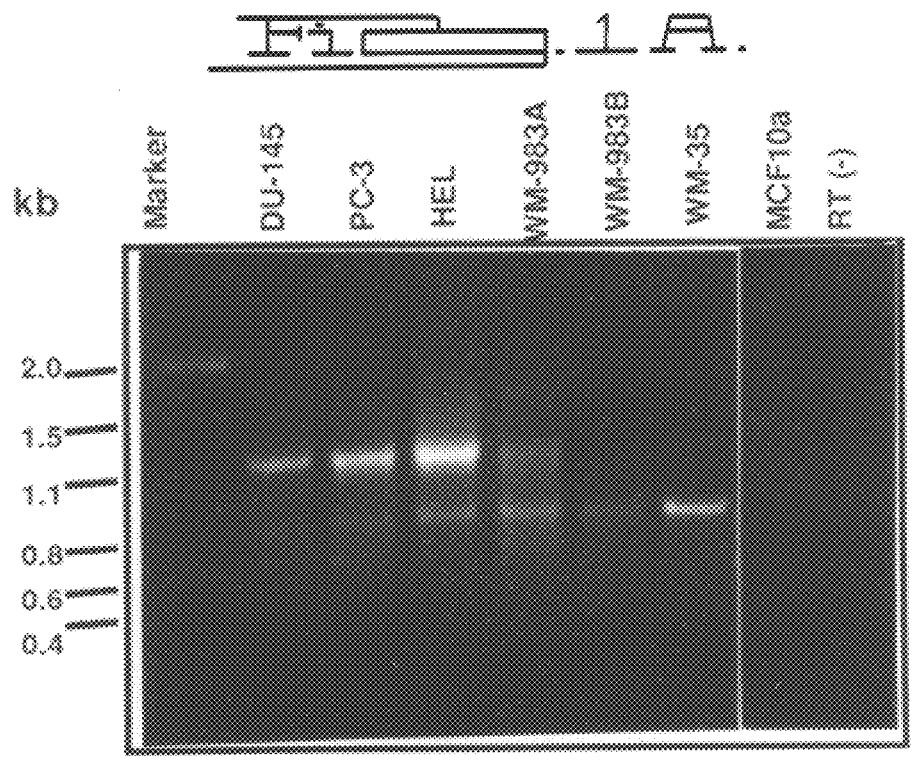
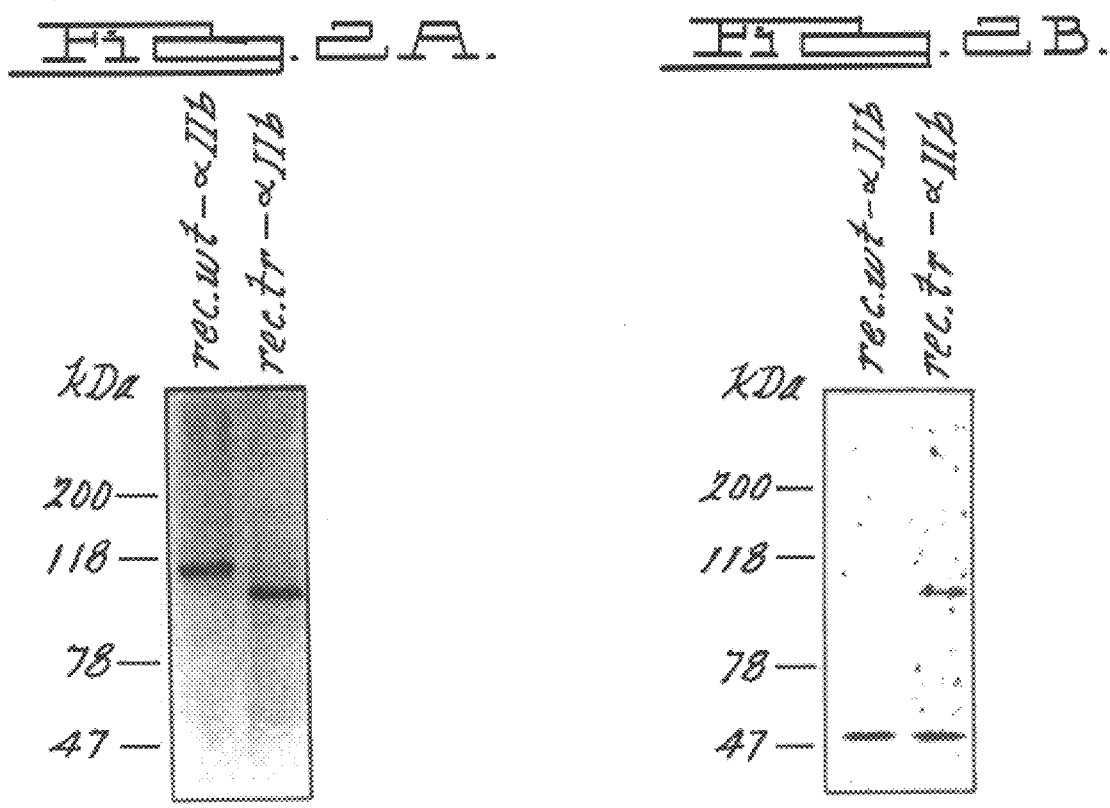

```
         10         20         30         40         50
GCAGATACGG AGCAAGAACA GCCAGAATCC AAACAGCAAG ATTGTGCTGC
         60         70         80         90        100
TGGACGTGCC GGTCCGGGCA GAGGCCCAAG TGGAGCTGCG AGGGAACTCC
        110        120        130        140        150
TTTCCAGCCT CCCTGGTGGT GGCAGCAGAA GAAGGTGAGA GGGAGCAGAA
        160        170        180        190        200
CAGCTTGGAC AGCTGGGGAC CCAAAGTGGA GCACACCTAT GAGCTCCACA
        210        220        230        240        250
ACAATGGCCC TGGGACTGTG AATGGTCTTC ACCTCAGCAT CCACCTTCCG
        260        270        280        290        300
GGACAGTCCC AGCCCTCCGA CCTGCTCTAC ATCCTGGATA TACAGCCCCA
        310        320        330        340        350
GGGGGGCCTT CAGTGCTTCC CACAGCCTCC TGTCAACCCT CTCAAGGTGG
        360        370        380        390        400
ACTGGGGGCT GCCCATCCCC AGCCCCTCCC CCATTCACCC GGCCCATCAC
        410        420        430        440        450
AAGCGGGATC GCAGACAGAT CTTCCTGCCA GAGCCCGAGC AGCCCCTGAG
        460        470        480        490        500
GCTTCAGGAT CCAGTTCTCG TAGTGAGCAG GCTCTCTGGT CTCTGGCCCG
        510        520        530        540        550
GCCTCCCCGG GACCCACGGG GCAGAGGGGA TGGGAGGAGG GAGAGGGGTC
        560        570        580        590        600
CGGGTGTGCT GTGGGCCTCT GTGGGCCACG CTTGGTCCCT GGGAGCACTT
        610        620        630        640        650
CAAGTGAACA TGGAGGAGCA TGCTGGCTTG TGTCTGGGGT GAGCTGAAAG
        660        670        680        690        700
ACACTTGCAC TTTTTAAAAG CTTCCCAGTA CGTTAAGGAG CATAAAACAA
        710        720        730        740        750
TGCCAAAGCA AGGTTAAAAA AAAAAAAAAA AAGTACTAG TCGACGGGTG
GCC
```

FIG. 1B

```
             350        360        370        380        390        400
tr-αIIb  AGGTGG ACTGGGGGCT GCCCATCCCC AGCCCCTCCC CCATTCACCC GGCCCATCAC
                                                           10920
gn-αIIb  AGGTGG ACTGGGGGCT GCCCATCCCC AGCCCCTCCC CCATTCACCC GGCCCATCAC 410        420        430        440        450        460
tr-αIIb  AAGCGGGATC GCAGACAGAT CTTCCTGCCA GAGCCCGAGC AGCCCTCGAG GCTTCAGGAT
                                           10960                  10980
gn-αIIb  AAGCGGGATC GCAGACAGAT CTTCCTGCCA GAGCCCGAGC AGCCCTCGAG GCTTCAGGAT 470        480        490        500        510        520
tr-αIIb  CCAGTTCTCG TAGTGAGCAG GCTCTCTGTT CTCTGGCCCG GCCTCCCCGG GACCCACGGG
                    11000                            11020                11040
gn-αIIb  CCAGTTCTCG TAGTGAGCAG GCTCTCTGTT CTCTGGCCCG GCCTCCCCGG GACCCACGGG 530        540        550        560        570        580
tr-αIIb  GCAGAGGGGA TGGGAGGAGG GAGAGGGGTC CGGGTGTGCT GTGGGCCTCT GTGGGCCACG
                    11060                            11080                11100
gn-αIIb  GCAGAGGGGA TGGGAGGAGG GAGAGGGGTC CGGGTGTGCT GTGGGCCTCT GTGGGCCACG 590        600        610        620        630        640
tr-αIIb  CTTGGTCCCT GGGAGCACTT CAAGTGAACA TGGAGGAGCA TGCTGGCTTG TGTCTGGGGT
                    11120                            11140                11160
gn-αIIb  CTTGGTCCCT GGGAGCACTT CAAGTGAACA TGGAGGAGCA TGCTGGCTTG TGTCTGGGGT 650        660        670        680        690        700
tr-αIIb  GAGCTGAAAG ACACTTGCAC TTTTTAAAAG CTTCCCAGTA CGTTAAGGAG CATAAAACAA
                    11180                            11200                11220
gn-αIIb  GAGCTGAAAG ACACTTGCAC TTTTTAAAAG CTTCCCAGTA CGTTAAGGAG CATAAAACAA 710        720        730        740        750
tr-αIIb  TGCCAAAGCA AGGTTAAAAA AAAAAAAAAA AAAGTACTAG TCGACCCGTG GCC
                    11240
gn-αIIb  TGCCAAAGCA AGGTTA
```

FIG. 1C

```
  1         10         20         30         40         50         60
QIRSKNSQNP NSKIVLLDVP VRAEAQVELR GNSFPASLVV AAEEGEREQN SLDSWGPKVE
           70         80         90        100        110        120
HTYELHNNGP GTVNGLHLSI HLPGGQSQPSD LLYILDIQPQ GGLQCFPQPP VNPLKVDWGL
          130        140        150        160        170        180
PIPSPSPIHP AHHKRDRRQI FLPEPEQPSR LQDPVLV|SR LSGLWPGLPG THGAEGMGGG
          190        200
RGVRVCCGPL WATLGPWEHF K*
```

FIG. 1E

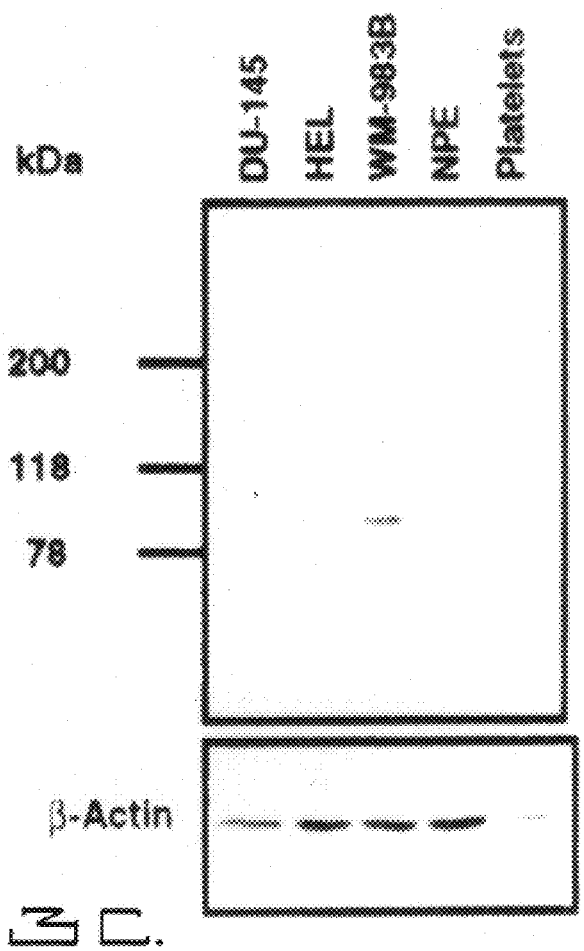
FIG. 3C.
FIG. 3D.
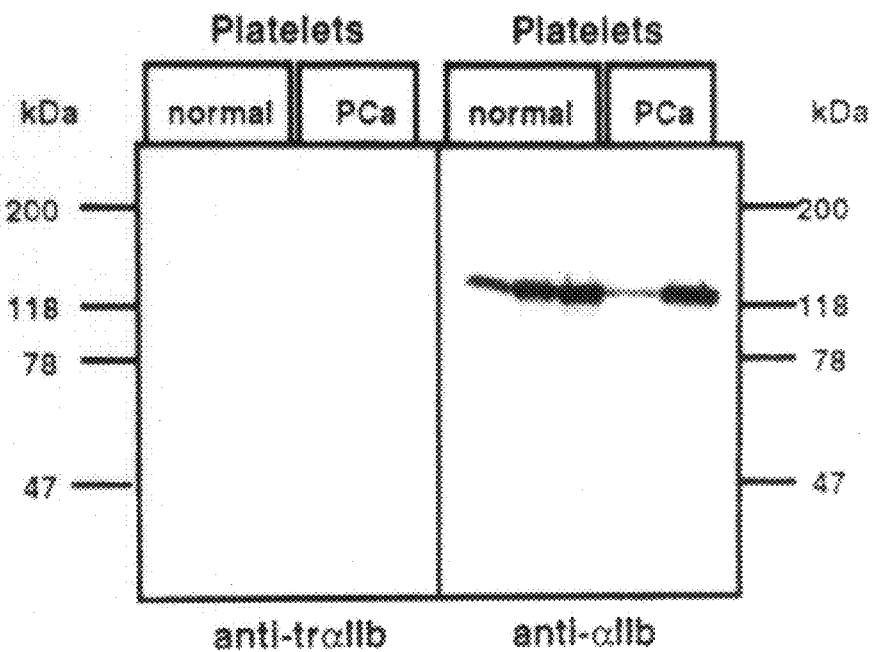

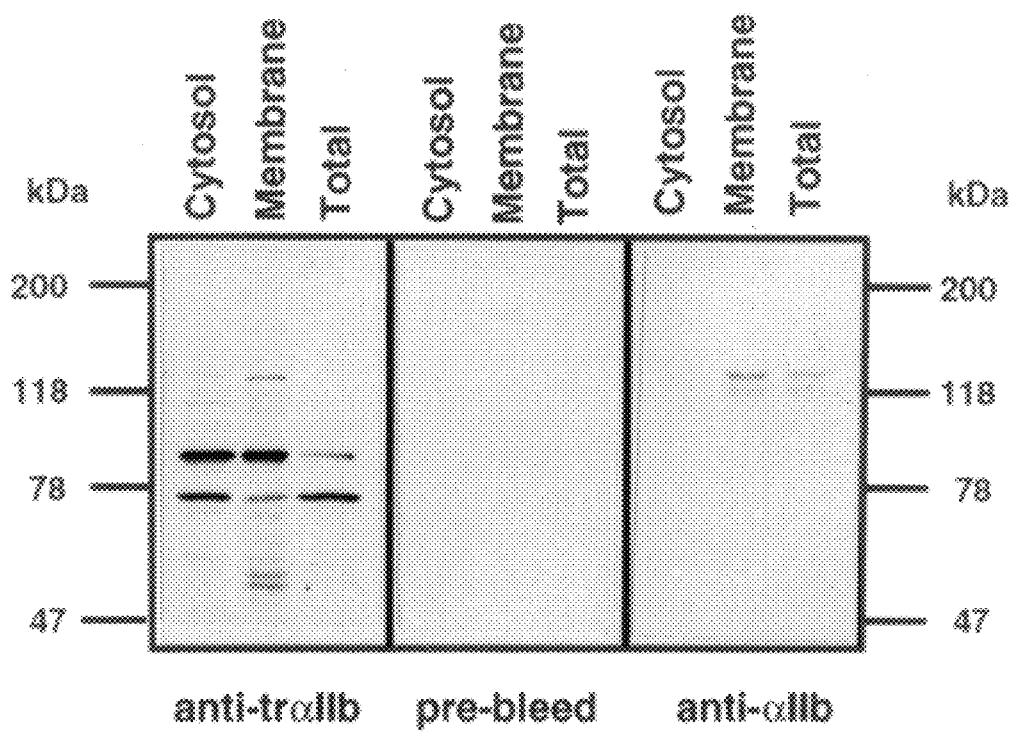
FIG. 5A.
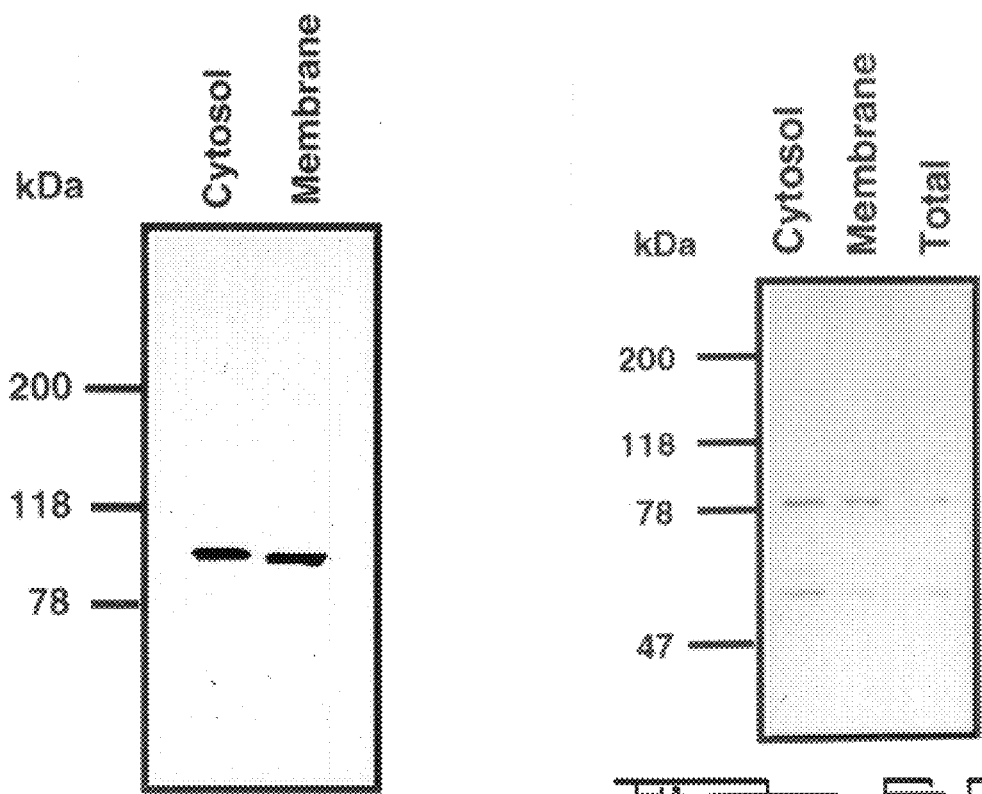
FIG. 5B.
FIG. 5C.

NUCLEIC ACID ENCODING TRUNCATED INTEGRINS

SPONSORSHIP

Work on this invention was supported in part by the National Institutes of Health Grant Nos. RO1-CA47115 and CA69845. The Government has certain rights in the invention.

FIELD OF THE INVENTION

The present invention relates generally to truncated integrins and more particularly, an isolated, soluble, truncated integrin, exclusively expressed in tumor cells.

BACKGROUND OF THE INVENTION

Tumor cell metastasis is a complex multistep process involving homotypic and heterotypic interactions among tumor cells and host cells (i.e., platelets, endothelial cells, etc.), in addition to tumor cell interactions with the extracellular matrix. These interactions are mediated by a variety of cell surface receptors including cadherins, selecting, and integrins. Tang, D. G. et al., *Invasion Metastasis* 95:109–122 (1994).

Integrins are heterotypic adhesion receptors involved in cell-cell and cell-matrix interactions. At least 15 alpha ($\alpha$) and 8 beta ($\beta$) subunits have been identified that can pair differently to form more than 20 receptors. Hynes, R. O., *Cell* 69:11–25 (1992); Schwartz, M. A., et al., *Ann. Rev. Cell Dev. Biol.* 11:549–599 (1995). Most cDNAs coding for the known integrins have been cloned and sequenced, and their genes localized to chromosomes. (Block, K. L. et al., *Stem Cells* 13:135–145 (1995).

The platelet integrin $\alpha IIb\beta 3$ (also known as GP llb-llla) is the prototypical integrin receptor and its structure has been studied in great detail. Calvete, J. J., *Throm. Haemostasis* 72:1–15 (1994). Integrins generally contain a large extracellular domain formed by the $\alpha$ (~1,000 amino acids) and $\beta$ (~750 amino acids) subunit, a single transmembrane segment from each subunit, and two short cytoplasmic tails, with the exception of $\beta 4$, whose cytoplasmic tail is more than 1,000 amino acid residues in length. Sastry, S. K. et al., *Current Opin. Cell Biol.* 5:819–831 (1993). The $\beta$ subunit is a single chain polypeptide with 4 cysteine repeats in the extracellular domain. The $\alpha$ subunit is a single gene product that is postranslationally cleaved into the light and heavy chain which are re-connected by a disulfide bond. The light chain of the $\alpha$ subunit contains the transmembrane and the cytoplasmic tail. Even though integrins were originally thought to function purely as anchor molecules, they are also known as signaling receptors. Integrin cytoplasmic tails do not have intrinsic enzymatic activity, but by recruiting and activating tyrosine (pp125FAK, pp60src), serine (PKCa, ERK, JNK, ILK) or lipid (cPLA2, PI3K, PI4P5K) kinases, they can simultaneously control multiple signaling pathways such as the MAP kinase and JAK-TAT pathways. Clark, E. A. et al., *Science* 268:233–2239 (1995); Schwartz, M. A. et al., *Annu. Rev. Cell Dev. Biol.* 11:549–599 (1995).

Human and rat cDNAs of $\alpha IIb$ as well as human cDNA of $\beta 3$ have been cloned. Poncz, M. et al., *J. Biol. Chem.* 262:8476–8482 (1987); Poncz, M. et al., *Blood* 75:1282–1289 (1990); Fitzgerald, L. et al., *J. Biol. Chem* 62:3936–3939 (1987). Genes of human $\alpha IIb$ and $\beta 3$ have been localized to chromosome 17, and their structures have been determined. Heidenreich, R. et al., *Biochem.* 29:1232–1244 (1990); Lanza, F. et al., *J. Biol. Chem.* 265:18098–18103 (1990); Bray, P. F. et al., *J Clin. Invest.* 80:1812–1817 (1987); Sosnoski, D. M. et al.,*J. Clin. Invest.* 81:1993–1998 (1988); Rosa, J. P. et al., *Blood* 72:593–600 (1988). The integrin $\alpha IIb$ gene is believed to be under stringent megakaryocyte specific transcriptional control whereas $\beta 3$ is widely expressed. Prandini, M. H. et al., *J. Biol. Chem.* 267:10370–10374 (1992); Calvete, J. J. et al., *Throm. Haemostasis* 72:1–15 (1994); Block, K. L. et al., *Stem Cells* 13:135–145 (1995).

Integrins are conformationally labile and they can exist in an inactive and 20 active form. The inactive integrin recognizes ligand with low affinity while the active integrin recognizes ligand with high affinity. For example, in resting platelets $\alpha IIb\beta 3$ is constitutively expressed in an inactive form, and only after platelet activation is the integrin converted to an active state which then binds plasma fibrinogen with high affinity, thereby resulting in platelet aggregation. Shattil, S. J. et al., *Current Opin. Cell Biology* 6:695–704 (1994). Integrins can be activated by extracellular signals such as divalent cations ($Mn^{2+}$, $Ca^{2+}$) or by treatment with certain activating mAbs. Schwartz, M. A. et al., *Annu. Rev. Cell Dev. Biol.* 11:549–599 (1995). Such activation induces a conformational change without involving cellular metabolism, a phenomenon referred to as "outside-in" signaling. On the other hand, growth factor-mediated activation of intracellular kinases and phosphatases can result in integrin activation, a phenomenon referred to as "inside-out" signaling. Integrins therefore participate in bi-directional signaling. Schwartz, M. A. et al., *Annu. Rev. Cell Dev. Biol.* 11:549–599 (1995). Several reports in the literature indicate that inside-out signaling is mediated by the cytoplasmic tail of the $\alpha$ subunit, and outside-in signaling by the cytoplasmic tail of the $\beta$ subunit. Schwartz, M. A. et al., *Annu. Rev. Cell Dev. Biol.* 11:549–599 (1995); Shattil, S. J. et al., Current Opin. Cell Biology 6:695–704 (1994).

Although the relationship between integrin receptors and metastasis is variable, most integrins expressed by tumor cells are also expressed by their normal counterparts, however some tumor cells express certain integrins that are not expressed by their normal counterparts, a phenomenon referred to as "ectopic" or "abnormal" expression. For example, several groups have demonstrated the ectopic expression of $\alpha IIb\beta 3$ in non-megakaryocytic cells derived from solid tumors. Chen, Y. Q. et al., *J. Biol. Chem.* 267:17314–17320 (1992); Trikha, M. et al., *Cancer Res.* 56:5071–5078 (1996); Trikha, M. et al., *Cancer Res.* 57:2522–2528 (1997); Boekerche, H. et al., *Blood* 74:658–663 (1989); Kamiyama, M. et al., *Cancer Res.* 53:221–223 (1993); Chiang, H. S. et al., *Biochem. et Biophys. Acta* 1224:506–516 (1994); Puerschel, W. Ch. et al., *British J. Dermatol.* 135:883–887 (1996). This receptor participates in tumor cell-platelet, -endothelial cell, and -ECM interactions. Chiang, H. S. et al., *Biochim. et Biophys. Acta* 1224:506–516 (1996); Tang, D. G. et al., *Invasion Metastasis* 95:109–122 (1994); Honn, K. V. et al., *Exp. Cell Res.* 201:23–32 (1992). In addition, subpopulations from melanoma tumors, which differ in their metastatic potential, demonstrate a positive correlation between $\alpha IIb\beta 3$ expression and lung colony formation. Tang, D. G. et al., *Intl. J. Cancer* 54:338–347 (1993). Two mAbs directed to $\alpha IIb\beta 3$, 10E5 and PAC-1, inhibit lung colonization of tail vein injected human prostate adenocarcinoma DU-145 cells in SCID mice. Trikha, M. et al., *Prostate* In Press (1997). Collectively, these findings suggest that the platelet $\alpha IIb\beta 3$ integrin is ectopically expressed in non-megakaryocytic lineage tumor cells, and it participates in tumor cell metastasis. It is conceivable that as a result of transformation events transcription of the αIIb gene is elevated in some tumors which allows them to interact with the host in a platelet-type manner thereby facilitating the metastatic process. Recent studies indicate that human melanoma cells express an intracellular pool of constitutively active αIIbβ3, because these permeabilized cells recognize PAC-1, a unique mAb because it specifically recognizes the high affinity state of αIIbβ3 integrin. Shattil, S. J. et al., *J. Biol. Chem.* 260:11107–11114 (1995); Trikha, M. et al., *Cancer Res.* 57:2522–2528 (1997). Earlier reports in the literature indicate that CHO cells transfected with wt-αIIb and wt-β3 cDNAs constitutively express αIIbβ3 in a low affinity state. Schwartz, M. A. et al., *Annu. Rev. Cell Dev. Biol.* 11:549–599 (1995); O'Toole, T. E. et al., *J. Cell Biol.* 124:1047–1059 (1994). However, transfection with mutant αIIb constructs that either have a point mutation in the cytoplasmic tail or complete deletion of the tail, result in constitutive expression of the integrin in a high affinity state. Schwartz, M. A. et al., *Annu. Rev. Cell Dev. Biol.* 11:549–599 (1995); O'Toole, T. E. et al., *J. Cell Biol.* 124:1047–1059 (1994); O'Toole, T. E. et al., *Science* 254:845–847 (1991). To date no such naturally occurring mutant constructs had been observed.

SUMMARY OF THE INVENTION

An isolated, truncated integrin referred to herein as tr-αIIb, is provided. tr-αIIb is a novel, soluble, truncated integrin found to be exclusively expressed in tumor cells. An additional truncated integrin, tr-β3, has also been found to be exclusively expressed in tumor cells. Diagnostic compositions and methods for detecting tr-αIIb and tr-β3 to identify the presence of tumor cells in a sample are also provided.

Additional objects, advantages, and features of the present invention will become apparent from the following description and appended claims, taken in conjunction with the accompanying drawings.

BRIEF DESCRIPTION OF THE DRAWINGS

The various advantages of the present invention will become apparent to one skilled in the art by reading the following specification and subjoined claims and by referencing the following drawings in which:

FIG. 1A is an ethidium bromide-stained agarose gel showing the products of PCR amplification of an alternately spliced tr-αIIb cDNA;

FIG. 1B is a nucleotide sequence of the 1.1 kb product of tr-αIIb (SEQ ID NO:1);

FIG. 1C is a comparison of the partial nucleotide sequence of the 0.8 kb product with that of genomic αIIb IVS;

FIG. 1E is a partial amino acid sequence of tr-αIIb deduced from the cDNA (boxed amino acid sequence represents the region specific to tr-αIIb and the underlined amino acids represent the sequence used to generate the antibody to tr-αIIb) (SEQ ID NO:2);

FIG. 2A is an autoradiograph of the in vitro translation products for wt-αIIb and tr-αIIb;

FIG. 2B is an immunoblot of the in vitro translation products of wt-αIIb and tr-αIIb probed with an antibody to tr-αIIb;

FIG. 3C is an immunoblot of total cellular protein from DU-145, HEL and WM-983B human carcinoma cells and normal prostate epithelial cells and platelets. The blots were probed with antibody to tr-αIIb then stripped and probed with antibody to human actin;

FIG. 3D is an immunoblot of total cellular protein from healthy volunteers (normal) and patients with prostate adenocarcinoma (PCa) probed with antibody to tr-αIIb and wt-αIIb;

FIG. 5A is an immunoblot of the subcellular fractions of HEL cells probed with antibody to tr-αIIb, wt-αIIb or preimmune serum;

FIG. 5B is an immunoblot of the subcellular fractions of human melanoma WM983B cells probed with antibody to tr-αIIb;

FIG. 5C is an immunoblot of the subcellular fractions of WM983B cells probed with an antibody to tr-β3;

FIG. 6A is a schematic representation of the structure of a wild-type integrin;

FIG. 6B is a schematic representation of the structure of an integrin with wt-β3 and tr-αIIb subunits;

FIG. 6C is a schematic representation of the structure of an integrin with wt-αIIb and tr-β3 subunits;

FIG. 6D is a schematic representation of the structure of a fully truncated integrin having tr-αIIb and tr-β3 as its subunits;

DETAILED DESCRIPTION OF THE PREFERRED EMBODIMENTS

Figure 1D:
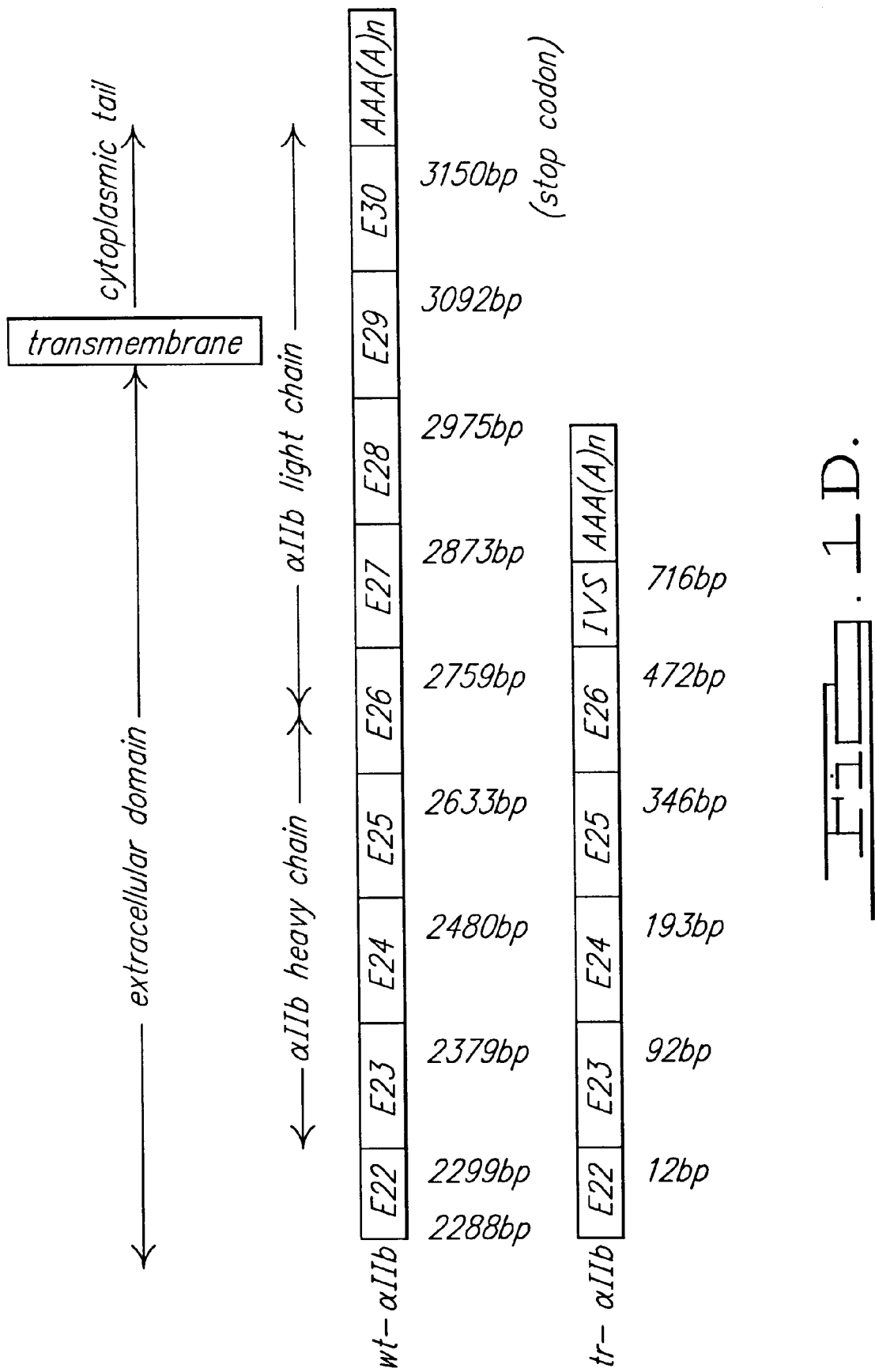
FIG. 1D is a schematic representation of the predicted structural comparison of wt-αIIb and tr-αIIb.

An isolated, alternately spliced variant of αIIb referred to herein as tr-αIIb, is provided. tr-αIIb contains exons 22 through 26 of wt-αIIb with exons 27 through 30 replaced with a partial sequence from intron 26, but lacks the transmembrane and cytoplasmic portions of the light chain. An antibody (referred to herein as pAb MTB1) generated to the unique sequence of tr-αIIb is also provided. pAb MTB1 recognizes tr-αIIb, but not wt-αIIb. Western blotting with pAb MTB1 identified an ~100 kDa tr-αIIb protein that is expressed in human leukemia, prostate adenocarcinoma, and melanoma cells, but not in platelets or normal prostate epithelial cells. In addition, it has been found that these melanoma and prostate adenocarcinoma cells also express an alternately spliced and truncated β3 (referred to herein as tr-β3) which also lacks the transmembrane and cytoplasmic domain. An antibody (referred to herein as pAb MTB4) generated to the unique sequence of tr-β3 is also provided. Unlike wt-αIIb and wt-β3, tr-αIIb and tr-β3 are expressed in both cytoplasmic and membrane compartments.

The nucleic acid sequence of the cDNA encoding tr-αIIb and its deduced amino acid sequence are set forth in SEQ ID NOS: 1 and 2, respectively. In a preferred embodiment, the isolated nucleic acid molecule of the invention comprises the nucleotide sequence of SEQ ID NO: 1, or homologues therefore. In another preferred embodiment, the isolated and purified polypeptide of the invention comprises the amino acid sequence of SEQ ID NO: 2, as well as biological equivalents.

In another embodiment, the isolated and purified nucleic acid molecule of the present invention is incorporated into an appropriate recombinant expression vector, e.g., viral or plasmid, which is capable of transfecting an appropriate host cell, either eukaryotic (e.g., mammalian) or prokaryotic (e.g., *E. coli*). Such nucleic acid molecules may involve alternate nucleic acid forms, such as cDNA, gDNA (genomic DNA), and DNA prepared by partial or total chemical synthesis. The nucleic acid molecule may also be accompanied by additional regulatory elements, such as promoters, operators and regulators, which are necessary and/or may enhance the expression of the protein encoded by the nucleic acid molecule. It is further contemplated that the nucleotide sequence of the present invention may be utilized to manufacture tr-αIIb using standard synthetic methods. Various expression vectors and methods for introducing such vectors into cells are known in the art and are described, for example, in Sambrook et al., *Molecular Cloning: A Laboratory Manual* (Cold Spring Harbor Laboratory Press, 1989).

In yet another embodiment, the present invention provides a recombinant host cell transfected with a vector of the present invention comprising the nucleic acid molecule of the present invention. Preferably, a recombinant host cell comprises a polynucleotide under the transcriptional control of regulatory signals functional in the recombinant host cell, wherein the regulatory signals appropriately control expression of the polynucleotide of the present invention in a manner to enable all necessary transcriptional and post-transcriptional modifications. The incorporation of these sequences into prokaryotic and eukaryotic host cells by standard transformation and transfection processes, thus provides for the production of encoded tr-αIIb protein.

In another aspect, DNA sequence information provided by the present invention allows for the preparation of relatively short DNA (or RNA) sequences or probes that are identical to or hybridize to the nucleotide sequence disclosed herein. Nucleic acid probes of an appropriate length are prepared based on a consideration of the nucleotide sequence of SEQ ID NO: 1 or to the nucleotide sequence of tr-β3 wherein said sequence is set forth in Fitzgerald, L. A. et al., *J. Biol. Chem.* 262:3936–3939 (1987) and Djaffar, I. et al., *Biochem. J.* 300:69–74 (1994) herein, expressly incorporated by reference. Fitzgerald et al. teaches the complete wild-type sequence of β3 (also known as glycoprotein IIIa) and Djaffar et al. discloses the 340 base pair insert at position 1281 of the wild-type sequence which results in tr-β3 integrin. The probes can be used in a variety of assays appreciated by those skilled in the art, for detecting the presence of complementary sequences in a given sample. The probes may be useful in prognostic and diagnostic applications.

A preferred nucleic acid sequence employed for hybridization studies or assays includes probe molecules that are complementary to at least a 10 to 70 or so long nucleotide stretch of the polynucleotide sequence shown in SEQ ID NO: 1 or to the nucleotide sequence of tr-β3. A size of at least 10 nucleotides in length helps to ensure that the fragment will be of sufficient length to form a duplex molecule that is both stable and selective. Molecules having complementary sequences over stretches greater than 10 bases in length are generally preferred in order to increase stability and selectivity of the hybrid, and thereby improve the quality and degree of specific hybrid molecules obtained. It will be appreciated that nucleic acid molecules having gene-complementary stretches of 25 to 40 nucleotides, 55 to 70 nucleotides, or even longer where desired, may be preferred. Such fragments can be readily prepared by, for example, directly synthesizing the fragment by chemical means, by application of nucleic acid reproduction technology, such as the PCR technology of U.S. Pat. No. 4,683,202, or by excising selected DNA fragments from recombinant plasmids containing appropriate inserts and suitable restriction enzyme sites. In certain embodiments, it is also advantageous to use oligonucleotide primers. The sequence of such primers is designed using the polynucleotide of the present invention and is used with PCR technology.

In one embodiment, the present invention provides an antibody immunoreactive with the tr-αIIb polypeptide. In another embodiment, the invention provides an antibody immunoreactive with the tr-β3 polypeptide. In a preferred embodiment, polyclonal antibody pAb MTB1 is provided, which is specific for tr-αIIb. In another preferred embodiment polyclonal antibody pAb MTB4, specific for tr-β3, is provided. Also contemplated by the present invention are antibodies immunoreactive with homologues or biologically equivalent polynucleotides and polypeptides of the present invention. As used herein, the term "antibody" is used in its broadest sense to include polyclonal and monoclonal antibodies, as well as polypeptide fragments of antibodies that retain a specific binding activity for tr-αIIb or tr-β3. One skilled in the art will appreciate that anti-tr-αIIb or anti-tr-β3 antibody fragments such as Fab, F(ab')$_2$ and Fv fragments can retain specific binding activity for tr-αIIb or tr-β3 and, thus, are included within the definition of an antibody. In addition, the term "antibody" as used herein includes naturally occurring antibodies as well as non-naturally occurring antibodies and fragments that retain binding activity. Methods of making antibodies are known in the art. See, e.g., Harlow and Lane, *Antibodies: A Laboratory Manual* (Cold Spring Harbor Press, 1988).

Diagnostic methods are further provided by the present invention and may be used to detect the presence of tr-αIIb and/or tr-β3 in a sample. In one embodiment, a method of detecting the presence of tr-αIIb in a sample is provided, wherein the method comprises the steps of administering to the sample a nucleic acid probe specific for tr-αIIb and detecting hybridization of the probe and nucleotide sequences encoding tr-αIIb in the sample. The methods used to detect the presence of tr-αIIb and/or tr-β3 may include, but are not limited to, amplification of the nucleic acid sequences encoding for tr-αIIb and/or tr-β3 by PCR or other methods known to those skilled in the art. In another embodiment, a method of detecting the presence of tr-β3 in a sample is provided comprising the steps of administering to the sample a nucleic acid probe specific for tr-β3 and detecting hybridization of the probe and nucleotide sequences encoding tr-β3 in the sample. Hybridization may be carried out under stringent conditions. The sample may be any suitable biological sample including, but not limited to, tissue, blood, semen and urine.

In yet another embodiment, the present invention contemplates a process of detecting a messenger RNA transcript that encodes the polypeptide of the present invention, wherein the process comprises (a) hybridizing the messenger RNA transcript with a polynucleotide sequence that encodes that polypeptide to form a duplex; and (b) detecting the duplex. Alternatively, the present invention provides a process of detecting a DNA molecule that encodes the polypeptide of the present invention, wherein the process comprises (a) hybridizing DNA molecules with a polynucleotide that encodes that polypeptide to form a duplex; and (b) detecting the duplex.

The present invention also provides methods of detecting the polypeptide of the present invention comprising the steps of immunoreacting the polypeptide with an antibody to form an antibody-polypeptide conjugate, and detecting the conjugate, e.g., conjugating the antibodies to chemiluminescent molecules such as dioxytane-based molecules known in the art, for use as labelled probes. Thus, methods of detecting tr-αIIb protein and/or tr-β3 protein in a sample are provided whereby antibody which specifically binds to tr-αIIb and/or tr-β3 is administered to a sample, and binding is detected. It will be appreciated by those skilled in the art that such immunoassay methods include, without limitation, radioimmunoassays, enzyme-linked immunosorbent assays, "sandwich" assays, precipitin reactions, gel diffusion immunodiffusion assays, agglutination assays and immunoelectrophoresis assays.

In yet another embodiment, the present invention provides a polypeptide or fragment thereof having the amino acid sequence of SEQ ID NO: 2, capable of binding antibodies to tr-αIIb. In another embodiment, the present invention provides a polypeptide or fragment thereof of the truncated integrin protein tr-β3 capable of binding antibodies specific to tr-β3. Preferably, the antibody is sequestered from a sample on a solid support. The polypeptide may comprise an indicator for conjugate detection, e.g., a chromophore, fluorophore, biotin moeity or an enzyme.

In another aspect, the present invention contemplates a diagnostic assay kit for detecting the presence of tr-αIIb and/or tr-β3 in a biological sample, wherein the kit comprises a first container containing a first antibody or antibodies capable of immunoreacting with the polypeptide that comprises tr-αIIb and/or tr-β3, with the first antibody present in an amount sufficient to perform at least one assay. Preferably, an assay kit of the invention further comprises a second container containing a second antibody that immunoreacts with the first antibody. More preferably, the antibodies used in an assay kit of the present invention are monoclonal antibodies. Even more preferably, the first antibody is affixed to a solid support. More preferably still, the first and second antibodies comprise an indicator, and, preferably, the indicator is a radioactive label or an enzyme.

In an alternative aspect, the present invention provides a diagnostic assay kit for detecting the presence, in biological samples, of the polynucleotides of tr-αIIb and/or tr-β3. The kits comprise a container that contains a polynucleotide identical or complementary to a segment of at least 10 contiguous nucleotide bases of the polynucleotide of the present invention.

In another embodiment, the present invention contemplates a diagnostic assay kit for detecting the presence, in a biological sample, of an antibody immunoreactive with the tr-αIIb and/or tr-β3 polypeptides. The kits comprise a container containing the polypeptide that immunoreacts with the antibody, with the polypeptide present in an amount sufficient to perform at least one assay.

It will be appreciated that the nucleic and amino acid sequences of the present invention can include some variation from the sequences represented by and complementary to the sequences set forth in the Sequence Listing but must be substantially represented by or complementary to those set forth therein. By "substantially represented by" or "substantially complementary to" is meant that any variation therein does not impair the functionality of the sequence to any significant degree. As used herein, the term "nucleic acid" is intended to mean natural and synthetic linear and sequential arrays of nucleotides and nucleosides, e.g. in cDNA, genomic DNA (gDNA), mRNA, and RNA, oligonucleotides, oligonucleosides and derivatives thereof. It will also be appreciated that such nucleic acids can be incorporated into other nucleic acid chains referred to as "vectors" by recombinant-DNA techniques such as cleavage and ligation procedures. The terms "fragment" and "segment" are as used herein with reference to nucleic acids (e.g., cDNA, genomic DNA, i.e., gDNA) are used interchangeably to mean a portion of the subject nucleic acid such as constructed artificially (e.g. through chemical synthesis) or by cleaving a natural product into a multiplicity of pieces (e.g. with a nuclease or endonuclease to obtain restriction fragments). As used herein, "A" represents adenine; "T" represents thymine; "G" represents guanine; "C" represents cytosine; and "U" represents uracil.

As referred to herein, the term "encoding" is intended to mean that the subject nucleic acid may be transcribed and translated into the subject protein in a cell, e.g. when the subject nucleic acid is linked to appropriate control sequences such as promoter and enhancer elements in a suitable vector (e.g. an expression vector) and the vector is introduced into a cell. The term "polypeptide" is used to mean three or more amino acids linked in a serial array.

As referred to herein, the term "capable of hybridizing under high stringency conditions" means annealing a strand of DNA complementary to the DNA of interest under highly stringent conditions. Likewise, "capable of hybridizing under low stringency conditions" refers to annealing a strand of DNA complementary to the DNA of interest under low stringency conditions. In the present invention, hybridizing under either high or low stringency conditions would involve hybridizing a nucleic acid sequence (e.g., the complementary sequence to SEQ ID NO: 1 or portion thereof), with a second target nucleic acid sequence. "High stringency conditions" for the annealing process may involve, for example, high temperature and/or low salt content, which disfavor hydrogen bonding contacts among mismatched base pairs. "Low stringency conditions" would involve lower temperature, and/or lower salt concentration than that of high stringency conditions. Such conditions allow for two DNA strands to anneal if substantial, though not near complete complementarity exists between the two strands, as is the case among DNA strands that code for the same protein but differ in sequence due to the degeneracy of the genetic code. Appropriate stringency conditions which promote DNA hybridization, for example, 6×SSC at about 45° C., followed by a wash of 2×SSC at 50° C. are known to those skilled in the art or can be found in *Current Protocols in Molecular Biology*, John Wiley & Sons, NY (1989), 6.31–6.3.6. For example, the salt concentration in the wash step can be selected from a low stringency of about 2×SSC at 50° C. to a high stringency of about 0.2×SSC at 50° C. In addition, the temperature in the wash step can be increased from low stringency at room temperature, about 22° C., to high stringency conditions, at about 75° C. Other stringency parameters are described in Maniatis, T., et al., *Molecular Cloning: A Laboratory Manual*, Cold Spring Harbor Laboratory Press, Cold Spring N.Y., (1982), at pp.

387–389; see also Sambrook J. et al., *Molecular Cloning: A Laboratory Manual,* Second Edition, Volume 2, Cold Spring Harbor Laboratory Press, Cold Spring, N.Y. at pp. 8.46–8.47 (1989).

As used herein, the term "specifically binds" refers to a non-random binding reaction between two molecules, for example between an antibody molecule immunoreacting with an antigen.

SPECIFIC EXAMPLE 1

Results

Detection of wt-αIIb and tr-αIIb integrin cDNA. To conclusively demonstrate that platelet αIIb integrin is transcribed in non-megakaryocytic tumor cells, the full length αIIb cDNA from cell lines derived from solid tumors was sequenced. The 5'-region of the αIIb cDNA was amplified by 5'-RACE and published in Trikha, M. et al., *Prostate* (In Press, 1997). The remaining 1.1 kb of the αIIb cDNA was amplified by 3'-RACE. In addition to the expected 1.1 kb fragment, there is a novel PCR fragment of ~0.8 kb expressed in human prostate adenocarcinoma, leukemia, and melanoma cells (FIG. 1). The PCR products result from reverse transcribed poly A RNA and not contaminating genomic DNA based on the following reasons. First, RNA treated with DNase I was used for RT, second, Oligo dT primers were used for RT, third no amplification was obtained in the absence of RTase, fourth, control reactions lacking template result in no amplification, fifth, no PCR product is obtained from RNA from normal cells, and sixth, no PCR product is obtained in the absence of a primer (FIG. 1A). The sequence of the 1.1 kb PCR fragment, which spans exons 22 through 30 and the 3'UTR, is identical to wt-αIIb (2,288 bp–3,333 bp; Frachet, P. et al., *Mol. Biol. Rep.* 14:27–33 (1990)). Sequencing of the ~0.8 kb PCR product revealed it to be an alternately spliced product containing exons 22 through 26, with exons 27 through 30 replaced by a partial sequence from intron 26 (11,000 bp–11,243 bp; Heidenreich, R. et al., *Biochemistry* 29:1232–1244 (1990)) and the poly A tail (FIG. 1C). A schematic representation of the structure of wt-αIIb (1.1 kb) and alternately spliced tr-αIIb (~0.8 kb) is shown in FIG. 1D.

Northern blotting of human prostate, leukemia, and melanoma mRNA with the alternately spliced tr-αIIb cDNA as a probe (data not shown) or with a wt-αIIb probe (Trikha, M. et al, *Cancer Res.* 57:2522–2528 (1997); Trikha, M. et al., *Prostate* In Press (1997)) reveals a single band that has a similar size as platelet αIIb mRNA. This result is attributed to the ~300 bp difference in molecular mass between wt-αIIb and tr-αIIb mRNA that cannot be resolved in this region of the gel. Altogether, these findings suggest that wt-αIIb and tr-αIIb are similar with the exception of exons 27–30.

Methods

3'-Rapid Amplification of cDNA ends (3'-RACE). Total RNA from tumor cells was obtained by the acid guanidinium isothiocyanate method using the Tri-Reagent kit (Molecular Research Center, Inc., Cincinnati, Ohio). To remove contaminating DNA, total RNA (2 μg) was treated with RNase free DNase I (Life Technologies, Gathersburg, Md.) in PCR buffer (20 mM Tris-HCl, pH 8.4, 50 mM KCl, 2.5 mM MgCl$_2$), and DNase I was neutralized with EDTA (1.2 mM, 65° C. for 15 min). RNA was reverse transcribed and amplified by using the 3'-RACE kit (Life Technologies). Briefly, cDNA synthesis was initiated by the addition of cDNA synthesis adaptor primer (AP: 5'-GGC CAC GCG TCG ACT AGT ACT TTT TTT TTT TTT TTT T-3', SEQ ID NO:3), and Superscript II for 50 min at 42° C. The reaction was terminated by incubation at 70° C. for 15 min followed by treatment with RNase H at 37° C. for 20 min. The RT mixture was amplified in a total volume of 50 μl of PCR buffer containing 250 ng of αIIb gene specific sense primer (5'-CTG GM GAG GCT GGG AGT C-3', SEQ ID NO:4), 200 nM of Abridged universal amplification primer (AUAP: 5'-GGC CAC GCG TCG ACT AGT AC-3', SEQ ID NO:5), 200 μM each of dATP, dCTP, dGTP, and dTTP, TaqStart antibody (Clontech, Palo Alto, Calif.), and Amplitaq DNA polymerase (Perkin-Elmer Cetus, Foster City, Calif.). PCR was performed in a GenAmp PCR system 9600 (Perkin-Elmer Cetus) by using the following conditions: one cycle of 94° C. for 10 s; thirty cycles of 94° C. for 20s, 55° C. 1 min, and 72° C. for 2 min, and one cycle of 72° C. for 7 min. An aliquot (1 μl) of the first round PCR product was reamplified under the exact conditions mentioned above with the substitution of the αIIb sense primer with a nested-αIIb sense primer (5'-GCA GAT ACG GAG CAA GAA CA-3', SEQ ID NO:6) and AUAP. PCR products were separated on a 1% agarose-TBE gel and visualized by ethidium bromide staining.

DNA sequencing. PCR products were separated on a 1% agarose-TAE gel and purified with the Qiagen kit (Chatsworth, Calif.). PCR products were directly sequenced by the Taq dyedeoxynucleotide Terminator Cycle Sequencing kit from Applied Biosystems (Foster City, Calif.) by employing the standard protocol on a Perkin Elmer thermal cycler (model 480). Sequencing reactions were run on a DNA sequencer (ABI, model 373), and the entire PCR product was sequenced by primer walking. Additionally, the PCR products were cloned into the pCR2.1 TOPO vector (Invitrogen, La Jolla, Calif.) and sequenced with T-7 and SP-6 primers. Sequencing was confirmed from several clones and different PCR products. The sequence was aligned to αIIb cDNA (Genbank accession number M34480; Frachet, P. et al., *Mol. Biol. Rep.* 14:27–33 (1990)), and genomic αIIb (Genbank accession number M33320; Heidenreich, R. et al., *Biochemistry* 29:1232–1244 (1990)) by using the MacVector™ 4.1 software on a Macintosh Quadra 630 computer.

SPECIFIC EXAMPLE 2

Results

Predicted structure of tr-αIIb. Theoretical translation of the alternate tr-αIIb product indicates that the protein contains only 7 amino acids from the light chain (151–157, FIG. 1E), thus it does not contain a transmembrane or cytoplasmic portion (FIG. 1D). Instead of the light chain, the tr-αIIb gene product contains 44 amino acids that map to αIIb intervening sequence (IVS) 11,000 bp–11,131 bp (Heidenreich, R. et al., *Biochem.* 29:1232–1244 (1990)), followed by a stop codon (αIIb IVS: 11,132 bp–11,134 bp). A peptide based on the unique sequence (171–200, FIG. 1E) that is specific to corresponding tr-αIIb and αIIb IVS, but is not expressed in wt-αIIb protein, was used to prepare a rabbit polyclonal antibody (pAb MTB1). The IgG fraction of pAb MTB1 was purified from the immunized serum by affinity chromatography on protein G and used for Western blotting as described below.

In vitro translation of recombinant wt-αIIb and tr-αIIb. To demonstrate that pAb MTB1 specifically recognizes tr-αIIb protein, but not wt-αIIb protein, recombinant wt- and tr-αIIb proteins were produced. In vitro translation of wt-αIIb pcDNA and tr-αIIb pcDNA vectors indicated single protein products for each that migrated under reducing conditions at molecular weights of ~120 kDa and ~100 kDa, respectively (FIG. 2A). Western blotting of the in vitro translated products with pAb MTB1 demonstrated that this Ab only recognizes tr-αIIb protein, but not wt-αIIb protein (FIG. 2B). Altogether, these results suggest that the reduced molecular weight of wt-αIIb and tr-αIIb is ~120 kDa and ~100 kDa, respectively, and pAb MTB1 recognizes tr-αIIb but not wt-αIIb.

Methods

Antibody preparations. A custom polyclonal antibody to tr-αIIb was prepared by Research Genetics Inc., Huntsville, Ala. The peptide (single letter amino acid code: THGAEGMGGGRGVRVCCGPLWATLGPWEHFK, SEQ ID NO:7) was conjugated to KLH, emulsified with an equal volume of Freund's Adjuvant and subcutaneously injected into rabbits. Primary immunization of 0.1 mg of peptide was followed by three successive boosts of 0.1 mg each. The third bleed with an ELISA titer for the peptide of 128,600 was used for all experiments, and the pre-immune bleed from the same rabbit was used as a negative control. The immunopure (G) IgG purification kit (Pierce, Rockford, Ill.) was used to purify the IgG fraction from the immunized rabbit serum and called pAb MTB1. Protein G eluant concentrations were monitored by Absorbance at 280 nm.

A custom antibody to tr-β3 was also prepared by Research Genetics as described above for the antibody to tr-αIIb with the exception of the peptide antigen. The peptide used to prepare anti-tr-β3 antibodies had the amino sequence CPGASVGTGPPFFLL (single letter amino acid code, SEQ ID NO:8).

Biotinylated antibodies were prepared using the protein biotinylation kit from Amersham (Arlington Heights, Ill.) according to the manufacturer's instructions.

Generation of wt-αIIb and tr-αIIb expression vectors. A primer (5'-GCC TCT AGA GCC ACC ATG GCC AGA GCT TTG TG-3, SEQ ID NO:9) that maps to 33 bp of HEL αIIb cDNA (Frachet, P. et al., *Mol. Biol. Rep.* 14:27–33 (1990)), and contains an XbaI restriction site, Kozak sequence, and an ATG sequence was used in conjunction with T-7 antisense primer (Invitrogen) to PCR amplify the predicted 3.3 kb αIIb insert from a pBluescript vector. The gel purified PCR product was digested with XbaI/HindIII and ligated into pcDNA 3.1 (−) vector (Invitrogen). Several clones were selected based on restriction mapping. Sequencing of the pcDNA 3.1 (−) construct revealed an insert which had complete homology to HEL αIIb cDNA from 33 bp–3,333 bp. Frachet, P. et al., *Mol. Biol. Rep.* 14:27–33 (1990). The tr-αIIb construct was developed by using the pCR2.1 TOPO II plasmid which contained the 3'-RACE product from PC-3 cells. Digestion of this plasmid by BamHI and EcoRI released an ~300 bp fragment which was specific to tr-αIIb. Meanwhile, a 2.7 kb αIIb fragment was cloned into pcDNA 3.1 (+) and digested with BamHI and EcoRI. The ~300 bp BamHI/EcoRI fragment was sub-cloned into the 2.7 kb αIIb pcDNA (+) vector. Sequencing of this construct revealed a recombinant cDNA which had complete homology to wt-αIIb (33 bp–2,759 bp) and contained the unique alternately spliced region specific to tr-αIIb (473–753 bp refer to FIG. 1B). This construct was regarded as the full length tr-αIIb pcDNA 3.1 (+) vector.

In vitro translation. The wt-αIIb pcDNA 3.1 (−) and the tr-αIIb pcDNA 3.1 (+) vectors were translated in vitro by the TNT-T7 Quick coupled Transcription/Translation System (Promega, Madison, Wis.). Briefly, 1 mg of DNA template, 2 ml of [$^{35}$S]methionine (1,000 Ci/mmole,) and 40 ml of the TNT/T7 rabbit reticulocyte lysate master mix was added to a final volume of 50 ml, and the reaction was incubated at 30° C. for 90 min. A 10% aliquot was mixed with 2× reducing sample buffer, boiled, electrophoresed on a 7.5% SDS-PAGE gel, transferred to nitrocellulose membrane, and the translated products were first visualized by autoradiography and then by Western blotting. The same blot was probed with pAb MTB1 and the bound antibody detected by anti-rabbit conjugated to HRP and ECL staining (Amersham).

SPECIFIC EXAMPLE 3

Results

Figure 3A:
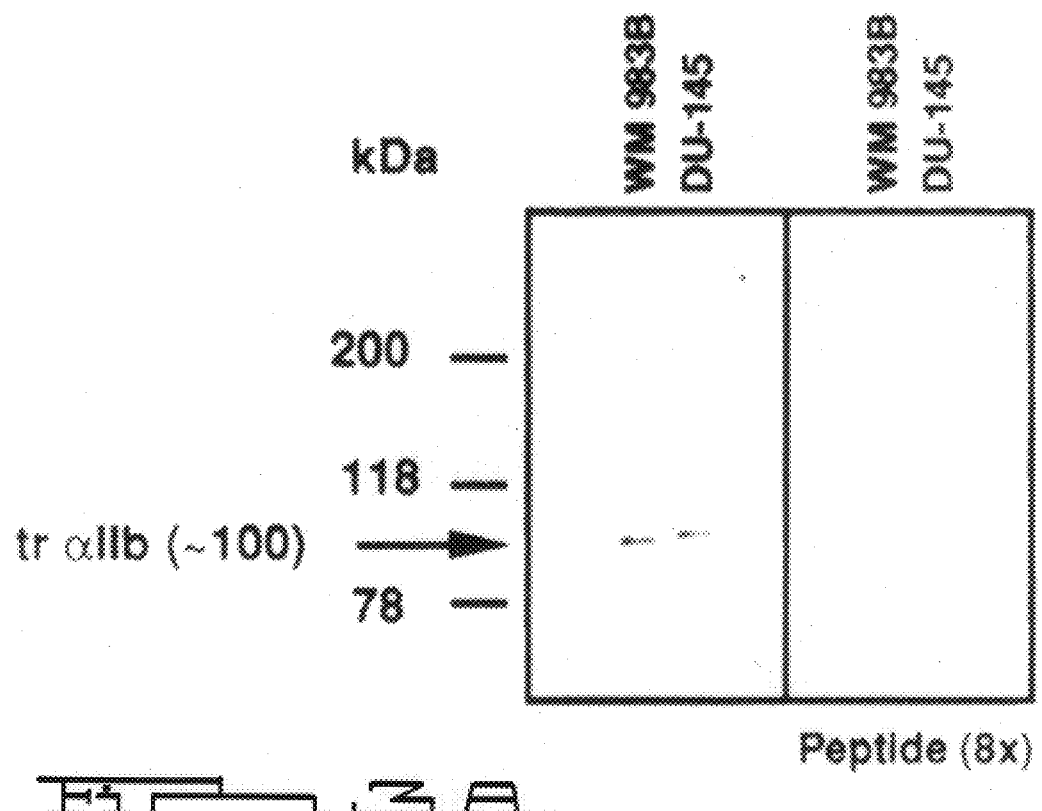
FIG. 3A is an immunoblot of the total cell lysate from human melanoma WM983 and prostate adenocarcinoma DU145 cells probed with an antibody to tr-αIIb in the absence and presence of excess antigen.
Figure 3B:
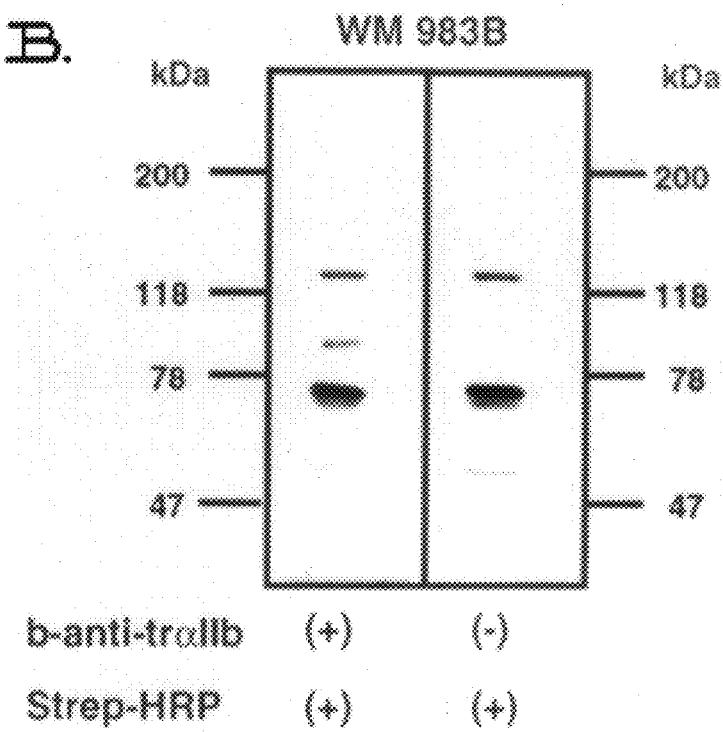
FIG. 3B is an immunoblot of the total cell lysate from human melanoma WM983 probed with a biotinylated antibody to tr-αIIb.
Figure 4:
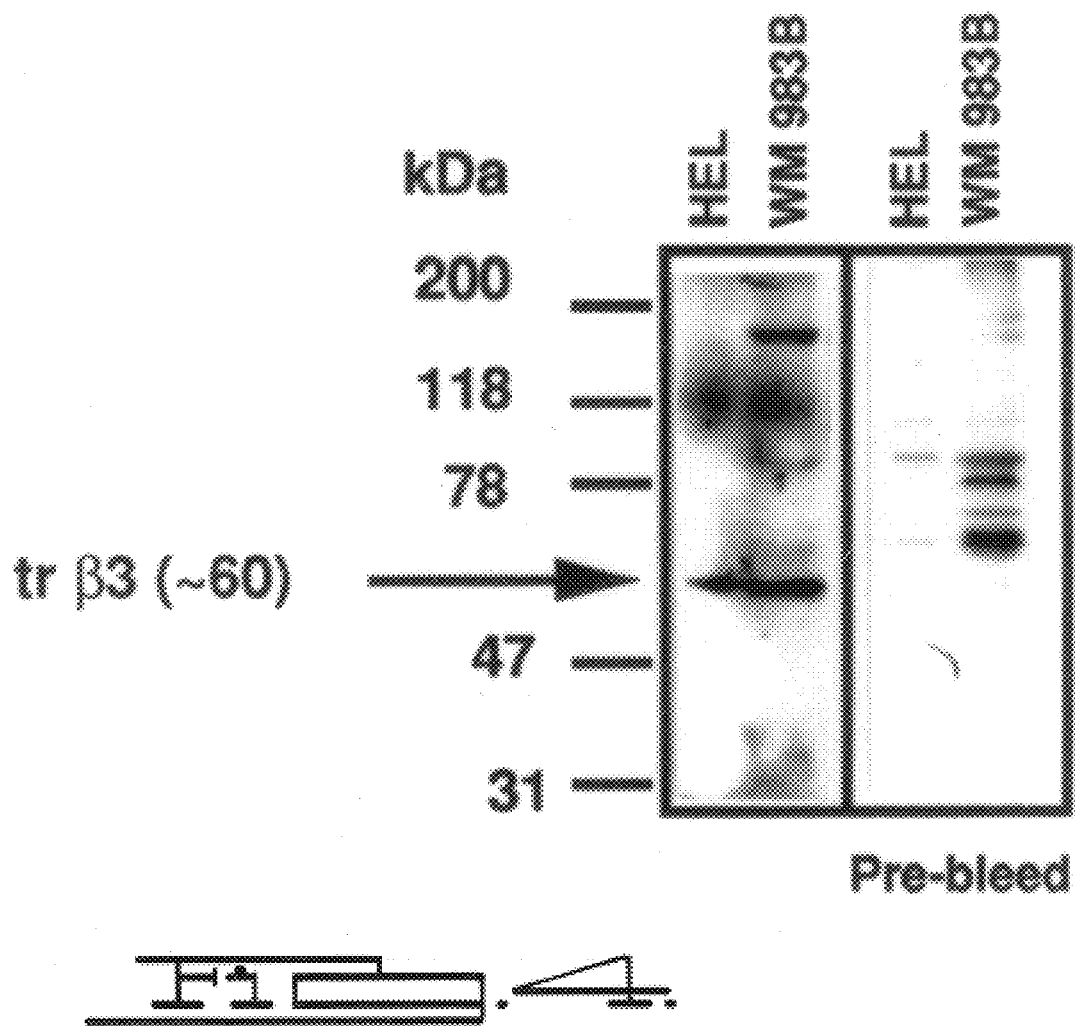
FIG. 4 is an immunoblot of total cell lysates from HEL and WM983B human carcinoma cells probed with either antibody to tr-β3 or with preimmune serum.
Figure 8A:
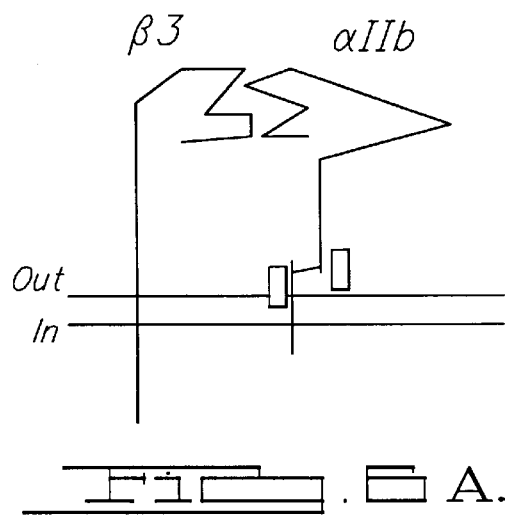
Figure 8B:
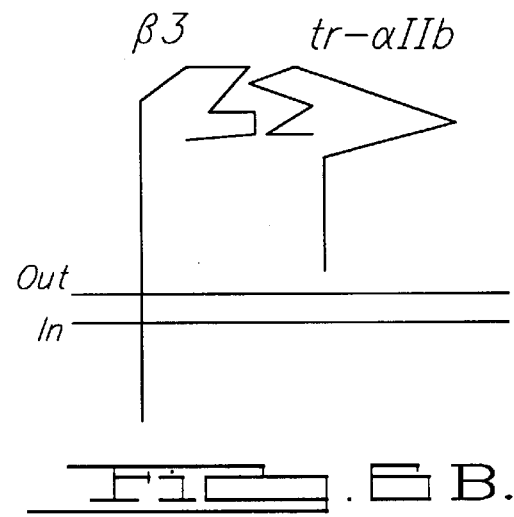
Figure 8C:
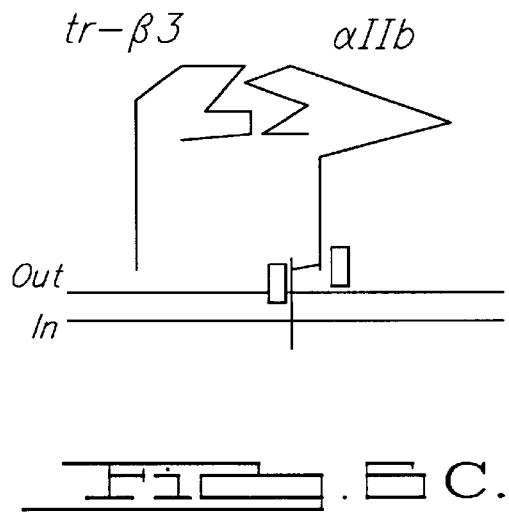
Figure 8D:
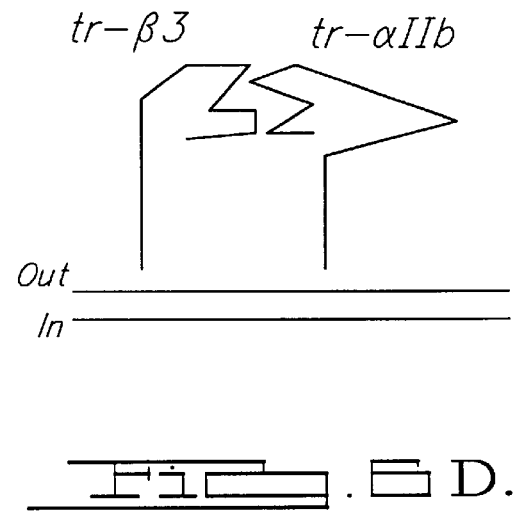

Detection of tr-αIIb and tr-β3 proteins in tumor cells. Earlier results indicate that a mAb directed to wt-αIIb detects ~120 kDa protein (reduced Mr of αIIb) that is expressed in prostate adenocarcinoma cells (Trikha, M. et al., *Cancer Res.* 56:5071–5078 (1996)), which confirms that wt-αIIb mRNA is translated in these cells. Thus, whether the alternately spliced tr-αIIb and tr-β3 mRNA was also translated in these tumor cells was studied. Western blotting of cell lysates from human tumor cells revealed that pAb MTB1 recognized a single band migrating at ~100 kDa (FIG. 3A) which is the Mr of in vitro translated recombinant tr-αIIb protein (Specific Example 2, FIG. 2). Excess antigen (8-fold molar excess over Ab) completely inhibited binding of pAb MTB1 (FIG. 3A), indicating that the ~100 kDa protein is immunologically related to the antigenic sequence. These results were confirmed when biotinylated-pAb MTB1 also recognized the same 100 kDa protein (FIG. 3B). The ~100 kDa protein recognized by pAb MTB1 is specifically expressed in prostate adenocarcinoma (DU-145), melanoma (WM-983B), erythroleukemia (HEL), but not in normal prostate epithelial cells (NPE) (FIG. 3C), or platelets from three healthy volunteers, or platelets from two patients with prostate adenocarcinoma (FIG. 3D). Stripping and reprobing the blot with mAb to human β-actin, and detecting the bound antibody with anti-mouse Ig conjugated to HRP and ECL staining, showed that the same amount of cellular protein was present for all samples. A rabbit pAb was raised to tr-β3 (herein referred to as pAb MTB4), as described in the Methods of Specific Example 2, and used in Western blotting. The results, similar to those obtained with tr-αIIb, indicate that non-megakaryocytic lineage cells express a unique protein with a Mr of ~60 kDa associated with the tr-β3 integrin protein (FIG. 4).

Since the predicted structure of tr-αIIb and tr-β3 lacks the transmembrane and cytoplasmic tail, whether these integrins could exist as soluble protein was examined. Subcellular fractionation of human erythroleukemia (HEL) and melanoma (WM 983B) cells followed by Western blotting with pAb MTB1 and pAb MTB4 indicated that tr-αIIb and tr-β3 are present in both cytosolic and membrane compartments (FIGS. 5A–5C). As expected, wt-αIIb could only be detected in total cell lysate and membrane fraction, but not in the cytosolic fraction (FIG. 5A). This data clearly indicates that tr-integrins can exist as transmembrane receptors as well as soluble receptors. A model is shown in FIG. 6. In this model the association of the truncated subunit with the wild type subunit would produce a membrane associated integrin. In contrast, association of tr-αIIb with tr-β3 (tr-αIIbβ3) would allow this complex to exist as a soluble receptor. Identification of the non-membrane associated soluble integrins of the present invention suggests a novel form of integrin regulation. Tumor cells may therefore utilize alternate splicing to switch an adhesion molecule such as an integrin into an anti-adhesion molecule also called disintegrin, and this phenomenon may be critically involved during the intravasation and extravasation steps of tumor cell dissemination.

Methods

Cells. Human prostate cancer cell lines, PC-3 and DU-145, isolated from metastatic lesions, and human erythroleukemia cell line HEL were obtained from American Type Culture Collection (Rockville, Md.). Human melanoma cell lines, WM 983A, WM 983B, and WM 35 were a gift from Dr. Meenhard Herlyn, The Wistar Institute (Philadelphia, Pa.). Normal breast epithelial cell line MCF10a was obtained from Karmanos Cancer Institute (Detroit, Mich.). These cell lines were cultured as described. Trikha, M. et al., Cancer Res. 56:5071–5078 (1996); Chen, Y. Q. et al., Int. J. Cancer 72:642–648 (1997). Normal prostate epithelial cells were a gift from Dr. Dharam Chopra, Wayne State University (Detroit, Mich.) or were purchased from Clonetics (San Diego, Calif.) and cultured in Clonetics medium. All experiments were performed with cells that were grown to approximately 80% confluency. Platelets from healthy volunteers or prostate adenocarcinoma patients were isolated from citrated blood as described. Trikha, M. et al., Throm. Res. 73:39–52 (1994).

Subcellular fractionation of total cellular proteins. Subcellular fractionation was performed as described. Hagman, W. et al., Prostaglandins 46:471–477 (1993). Briefly, tumor cells were washed in isotonic buffer (134 mM NaCl, 15 mM Tris-HCl, pH 7.6, 5 mM glucose, 1 mM EDTA, and 1 mM EGTA) and resuspended in homogenization buffer [25 mM Tris-HCL, pH 7.6, 1 mM EGTA, aprotinin (5 µg/ml), leupeptin (10 µg/ml), 1 mM PMSF]. The solution was sonicated (3×15 sec at 0° C.), centrifuged at 10,000×g for 15 min, and the resulting supernatant was recentrifuged at 100,000×g for 1 h at 4° C. The 100,000×g supernatant was removed and regarded as the cytosolic fraction. The pellet was rinsed and resuspended in homogenization buffer by sonication and regarded as the membrane fraction. Total protein was obtained by lysing cells with 20 mM Tris-HCl, pH 7.6, 150 mM NaCl, 0.5% NP-40, 0.5% Tween-20, 1 mM PMSF, aprotinin (5 µg/ml), and leupeptin (10 µg/ml), and 20 mM EDTA as described. Trikha, M. et al., Cancer Res. 56:5071–5078 (1996). Protein concentrations were determined by Bio-Rad's DC protein assay kit (Bio-Rad, Richmond, Calif.) and BCA protein Assay kit (Pierce).

Immunoblotting. Western blotting of freshly lysed solutions was performed as described. Trikha, M. et al., Cancer Res. 56:5071–5078 (1996). Briefly, cellular protein (20–60 µg) was mixed with an equal volume of 2× sample buffer (0.125M Tris, pH 6.8, 4% SDS, 20% glycerol, 20% 2-mercaptoethanol), boiled for 5 min, and electrophoresed on a 7.5% SDS-PAGE gel, and transferred to a nitrocellulose membrane. The αIIb integrin subunit was detected by mouse mAb MAB 1990 (10 ng/ml, Chemicon, Temecula, Calif.) as described. Trikha, M. et al., Cancer Res. 56:5071–5078 (1996). The tr-αIIb integrin subunit was detected by protein G purified pAb MTB1at a dilution of 1:2,000. Bound primary antibody was detected by species matched secondary Ig conjugated to HRP (1:1,500 dilution, Amersham, Arlington Heights, Ill.), and the bands were visualized by ECL detection (Amersham). Alternatively, pAb MTB1 was biotinylated (Amersham) and used as a primary Ab (1:2,000 dilution), followed by detection with Streptavidin conjugated to HRP (1:2,000 dilution) and ECL. The peptide antigen (8-fold molar excess) was preincubated with pAb MTB1 prior to Western blotting in order to compete out binding of the Ab to the membrane. Substitution of primary Ab with preimmune serum or absence of primary Ab served as negative controls.

SPECIFIC EXAMPLE 4

Results

Figure 7A:
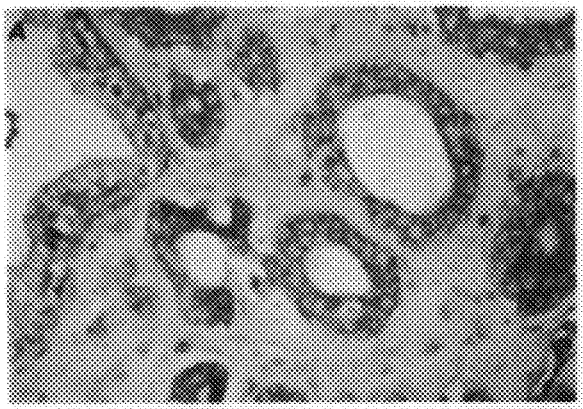
FIG. 7A is an immunohistogram of prostatic tumor tissue and normal prostatic tissue stained with antibody to tr-αIIb.
Figure 7B:
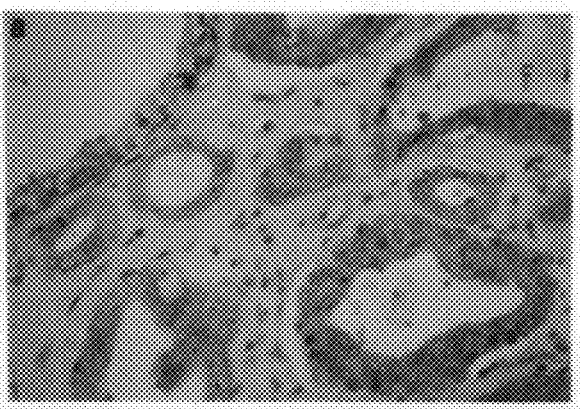
FIG. 7B is an immunohistogram of prostatic tumor tissue and normal prostatic tissue stained with preimmune serum for anti-tr-αIIb.
Figure 7C:
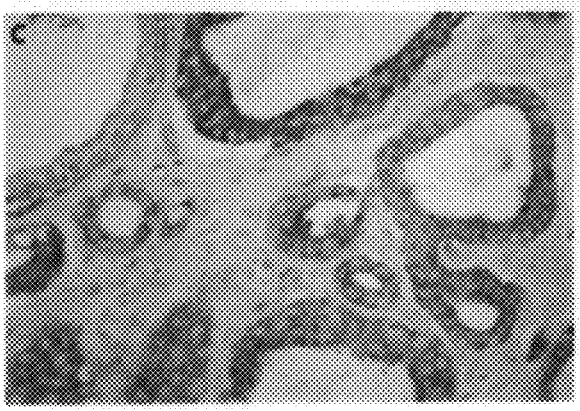
FIG. 7C is an immunohistogram of prostatic tumor tissue and normal prostatic tissue stained with antibody to tr-β3.
Figure 7D:
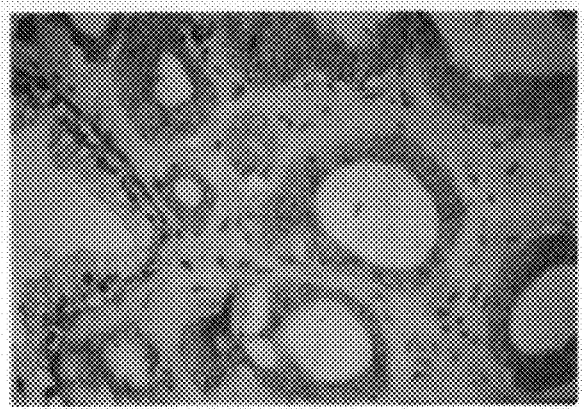
FIG. 7D is an immunohistogram of prostatic tumor tissue and normal prostatic tissue stained with preimmune serum for anti-tr-β3.

Immunohistochemical detection of tr-αIIb and tr-β3 in prostate adenocarcinoma tissue. The results described above indicate that tr-αIIb and tr-β3 integrins are expressed in cultured tumor cell lines. To confirm that expression of these integrins was not an artifact of in vitro cell culture, immunohistochemical staining of radical prostatectomy specimens obtained from patients who had undergone surgery for localized prostate adenocarcinoma was performed. Specimens from five patients indicated specific staining of pAb MTB1 and pAb MTB4 (described in the Methods of Specific Example 2) in prostate adenocarcinoma cells (brown color, FIGS. 7A, 7C). In normal prostatic tissue, pAb MTB1 and pAb MTB4 showed no immunoreactivity. Substitution of pAb MTB1 and pAb MTB4 with pre-immune serum (FIGS. 7B, 7D), served as a negative control. Results from these studies indicate that tr-αIIb and tr-β3 are not just expressed in cultured tumor cell lines, but are also expressed in prostate adenocarcinoma tumor tissue.

Methods

Immunohistochemistry. Representative formalin-fixed paraffin-embedded tissue sections were selected from radical prostatectomy specimens of patients who had undergone surgery for clinically localized adenocarcinoma of the prostate. All specimens were handled according to a previously described protocol. Sakr, W. A. et al., J. Urol. Path. 3:355–364 (1995). Sections were chosen to include normal and neoplastic tissue. The ABC method (Vector laboratories, Burlingame, Calif.) was used to visualize the binding of pAb MTB1, pAb MTB4 and the preimmune serum. Briefly, deparaffinized and blocked specimens were incubated with pAb MTB1 or pAb MTB4, or the pre-immune serum at a dilution of 1:100 for 1 h at room temperature. Following incubation, sections were washed and incubated with biotinylated anti-rabbit Ab (1:200 dilution) for 10 min, washed, and incubated with avidin-biotin complex peroxidase reagent and substrate for another 10 min. After color development the sections were counterstained with hematoxylin.

SPECIFIC EXAMPLE 5

Patients with metastatic disease may secrete the truncated integrins either locally or into the blood, serum or urine. The secreted proteins could thus be detected by an enzyme linked immunosorbent assay (ELISA), dot, and/or Western blotting techniques. In an ELISA, proteins are immobilized on 96-well ELISA plates, followed by the addition of antibody, e.g., pAb MTB1 or pAb MTB4, and goat anti-rabbit Ig antibody conjugated to Horse Radish Peroxidase (HRP). After the addition of the HRP-substrate, extent of color development is monitored by an ELISA plate reader. Trikha, M. et al., Cancer Res. 54:4993–4998 (1994). This approach quantitates the level of wild type- and tr-integrins which is then compared with stage and outcome of disease.

Expression of wild type and tr-integrin mRNAs in tumor specimens by In situ hybridization (ISH), RACE, and immunohistochemistry can also be determined. For ISH, sense and antisense riboprobes specific to the tr-integrin and the wild type integrin mRNAs are provided. Alternatively, a quantitative RT-PCR is used to compare the relative amount of gene expression of tr-integrin mRNAs in tumor versus normal tissue.

tr-integrins of the present invention may act as endogenous disintegrins and thereby confer a metastatic potential on tumor cells. The secreted integrin receptor could bind to extracellular matrix proteins and compete for binding with cell surface associated integrins. Since metastatic progression involves a change in the adhesive phenotype of tumor cells (Tang, D. G. et al., *Invasion Metastasis* 95:109–122 (1994)), expression of truncated integrins could make the tumor cells less adhesive and possibly more metastatic. Antimetastatic therapy based on drugs that neutralize the effect of integrins is thus also encompassed by the present invention. For example, such drugs could interfere with integrin function by inhibiting binding of the in vivo substrate to the integrin receptor and/or inhibiting association of the integrin subunits to form a functional receptor. These drugs could also target gene expression of the truncated integrins.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

All patents and other publications cited herein are expressly incorporated by reference.

We claim:
1. An isolated nucleic acid molecule encoding tr-αIIb, consisting of the nucleotide sequence of SEQ ID NO: 1.

\* \* \* \* \*

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
       (A) LENGTH: 753 base pairs
       (B) TYPE: nucleic acid
       (C) STRANDEDNESS: double
       (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:1:

```
GCAGATACGG AGCAAGAACA GCCAGAATCC AAACAGCAAG ATTGTGCTGC TGGACGTGCC        60

GGTCCGGGCA GAGGCCCAAG TGGAGCTGCG AGGGAACTCC TTTCCAGCCT CCCTGGTGGT       120

GGCAGCAGAA GAAGGTGAGA GGGAGCAGAA CAGCTTGGAC AGCTGGGGAC CCAAAGTGGA       180

GCACACCTAT GAGCTCCACA ACAATGGCCC TGGGACTGTG AATGGTCTTC ACCTCAGCAT       240

CCACCTTCCG GGACAGTCCC AGCCCTCCGA CCTGCTCTAC ATCCTGGATA TACAGCCCCA       300

GGGGGGCCTT CAGTGCTTCC CACAGCCTCC TGTCAACCCT CTCAAGGTGG ACTGGGGCT        360

GCCCATCCCC AGCCCCTCCC CCATTCACCC GGCCCATCAC AAGCGGGATC GCAGACAGAT       420

CTTCCTGCCA GAGCCCGAGC AGCCCTCGAG GCTTCAGGAT CCAGTTCTCG TAGTGAGCAG       480

GCTCTCTGGT CTCTGGCCCG GCCTCCCCGG GACCCACGGG GCAGAGGGGA TGGGAGGAGG       540

GAGAGGGGTC CGGGTGTGCT GTGGGCCTCT GTGGGCCACG CTTGGTCCCT GGGAGCACTT       600

CAAGTGAACA TGGAGGAGCA TGCTGGCTTG TGTCTGGGGT GAGCTGAAAG ACACTTGCAC       660

TTTTTAAAAG CTTCCCAGTA CGTTAAGGAG CATAAAACAA TGCCAAAGCA AGGTTAAAAA       720

AAAAAAAAAA AAAGTACTAG TCGACGCGTG GCC                                   753
```

(2) INFORMATION FOR SEQ ID NO:2:

(i) SEQUENCE CHARACTERISTICS:
       (A) LENGTH: 201 amino acids
       (B) TYPE: amino acid
       (C) STRANDEDNESS: unknown
       (D) TOPOLOGY: unknown (ii) MOLECULE TYPE: protein (xi) SEQUENCE DESCRIPTION: SEQ ID NO:2:

```
Gln Ile Arg Ser Lys Asn Ser Gln Asn Pro Asn Ser Lys Ile Val Leu
  1               5                  10                  15

Leu Asp Val Pro Val Arg Ala Glu Ala Gln Val Glu Leu Arg Gly Asn
             20                  25                  30

Ser Phe Pro Ala Ser Leu Val Val Ala Ala Glu Glu Gly Glu Arg Glu
             35                  40                  45

Gln Asn Ser Leu Asp Ser Trp Gly Pro Lys Val Glu His Thr Tyr Glu
     50                  55                  60

Leu His Asn Asn Gly Pro Gly Thr Val Asn Gly Leu His Leu Ser Ile
 65                  70                  75                  80

His Leu Pro Gly Gln Ser Gln Pro Ser Asp Leu Leu Tyr Ile Leu Asp
                 85                  90                  95

Ile Gln Pro Gln Gly Gly Leu Gln Cys Phe Pro Gln Pro Pro Val Asn
                100                 105                 110

Pro Leu Lys Val Asp Trp Gly Leu Pro Ile Pro Ser Pro Ser Pro Ile
                115                 120                 125

His Pro Ala His His Lys Arg Asp Arg Gln Ile Phe Leu Pro Glu
130                 135                 140

Pro Glu Gln Pro Ser Arg Leu Gln Asp Pro Val Leu Val Ser Arg
145                 150                 155                 160

Leu Ser Gly Leu Trp Pro Gly Leu Pro Gly Thr His Gly Ala Glu Gly
                165                 170                 175

Met Gly Gly Gly Arg Gly Val Arg Val Cys Cys Gly Pro Leu Trp Ala
                180                 185                 190

Thr Leu Gly Pro Trp Glu His Phe Lys
                195                 200

(2) INFORMATION FOR SEQ ID NO:3:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:3:

GGCCACGCGT CGACTAGTAC TTTTTTTTTT TTTTTTT                               37

(2) INFORMATION FOR SEQ ID NO:4:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:4:

CTGGAAGAGG CTGGGAGTC                                                   19
```

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:5:

GGCCACGCGT CGACTAGTAC                                                 20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:6:

GCAGATACGG AGCAAGAACA                                                 20

(2) INFORMATION FOR SEQ ID NO:7:

(i) SEQUENCE CHARACTERISTICS:
        (A) LENGTH: 31 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:7:

Thr His Gly Ala Glu Gly Met Gly Gly Arg Gly Val Arg Val Cys
1            5                   10                15

Cys Gly Pro Leu Trp Ala Thr Leu Gly Pro Trp Glu His Phe Lys
          20                 25                 30

(2) INFORMATION FOR SEQ ID NO:8:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:8:

Cys Pro Gly Ala Ser Val Gly Thr Gly Pro Pro Phe Phe Leu Leu
1            5                   10                15

(2) INFORMATION FOR SEQ ID NO:9:

(i) SEQUENCE CHARACTERISTICS:
        (A) LENGTH: 32 base pairs
        (B) TYPE: nucleic acid
        (C) STRANDEDNESS: single

```
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:9:

GCCTCTAGAG CCACCATGGC CAGAGCTTTG TG                                    32
```